United States Patent [19]

Kitko

[11] 4,249,274

[45] Feb. 10, 1981

[54] APPARATUS FOR SANITIZING TOILETS

[75] Inventor: David J. Kitko, Cincinnati, Ohio

[73] Assignee: The Procter & Gamble Company, Cincinnati, Ohio

[21] Appl. No.: 99,356

[22] Filed: Dec. 3, 1979

Related U.S. Application Data

[62] Division of Ser. No. 972,318, Dec. 22, 1978, Pat. No. 4,200,606.

[51] Int. Cl.³ ............... E03D 9/02; E03D 9/03; A61L 1/00
[52] U.S. Cl. ............................. 4/227; 4/228; 4/DIG. 9; 422/37
[58] Field of Search ............... 422/37, 266; 4/227, 4/228, DIG. 9

[56] References Cited

U.S. PATENT DOCUMENTS

| | | | |
|---|---|---|---|
| 1,798,090 | 3/1931 | Lebeque | 4/228 UX |
| 3,121,236 | 2/1964 | Yadro et al. | 4/228 |
| 3,243,377 | 3/1966 | Stolar | 252/100 |
| 3,318,815 | 5/1967 | Remler et al. | 252/106 |
| 3,339,801 | 9/1967 | Hronas | 4/228 X |
| 3,341,074 | 9/1967 | Pannutti | 4/227 X |
| 3,355,392 | 11/1967 | Cantor et al. | 252/99 |
| 3,378,495 | 4/1968 | Buck | 422/37 X |
| 3,444,566 | 5/1969 | Spear | 4/228 |
| 3,504,384 | 4/1970 | Radley et al. | 4/228 |
| 3,741,805 | 6/1973 | Crotly et al. | 422/37 X |
| 3,793,211 | 2/1974 | Kohler | 252/99 |
| 3,831,205 | 8/1974 | Poley | 4/228 |
| 3,936,385 | 2/1976 | Cheng | 252/99 |
| 4,036,407 | 7/1977 | Slone | 4/228 X |

*Primary Examiner*—Barry Richman
*Attorney, Agent, or Firm*—Ronald L. Hemingway; Richard C. Witte

[57] ABSTRACT

A method and article for sanitizing toilets wherein a hypochlorite sanitizing agent and a dye selected from the group consisting of FD & C Blue No. 1 and FD & C Green No. 3 are dispensed from separate dispensing means into the toilet flush water. The dye is resistant to attack by the hypochlorite and therefore provides an aesthetically pleasing color to the bowl water during the time period between flushes.

3 Claims, No Drawings

APPARATUS FOR SANITIZING TOILETS

This is a division of application Ser. No. 972,318, filed Dec. 22, 1978, now U.S. Pat. No. 4,200,606 issued Apr. 29, 1980.

TECHNICAL FIELD

The present invention relates to the automatic sanitizing of flush toilets by the dispensing of certain water-soluble, triarylmethane dyes and a hypochlorite sanitizing agent to the toilet bowl with each flush. The dye is resistant to attack by the hypochlorite and therefore provides color to the bowl water during the time period between flushes.

BACKGROUND ART

This invention relates to a method of sanitizing a toilet bowl. More particularly, it relates to a method wherein a hypochlorite sanitizing agent and a water-soluble dye which is resistant to attack by hypochlorite are automatically dispensed from separate dispensing means to the toilet bowl during flushing. The water in the bowl at the end of the flush is colored by the dye, and because of the dye's resistance to attack by hypochlorite, the bowl water remains colored during the time interval between flushes.

Automatically dispensed toilet bowl cleaning and/or sanitizing products, which contain dyes to provide a visual signal to the user that product is being dispensed, are well known. Such products are sold in the United States under the brand names VANISH AUTOMATIC (Drackett Products), TY-D-BOL AUTOMATIC (Knomark, Inc.) and SANIFLUSH AUTOMATIC (Boyle-Midway). All of these products contain dyes which provide a color to the toilet bowl water which persists between flushes, however, none of them contain a hypochlorite sanitizing agent or any other type of strong oxidant.

U.S. Pat. No. 3,504,384, Radley et al., issued Apr. 7, 1970, discloses a dual compartment dispenser for automatically dispensing a hypochlorite solution and a surfactant/dye solution to the toilet bowl during flushing. The dye which is taught in the patent is Disulfide Blue VN150. It is believed that the dye referred to in Radley et al. is acutally Disulphine Blue VN150 (Color Index No. 42045). This dye has been found to be resistant to oxidation to a colorless state by hypochlorite. However, this dye has a tendency to change from a blue to a reddish purple color upon prolonged contact with hypochlorite.

A persistant color in the toilet bowl water is aesthetically pleasing. Moreover, when the dispensing of hypochlorite and dye into the toilet are properly coordinated with each other so that dye is only dispensed when hypochlorite is dispensed, the color in the bowl water serves to assure the consumer that the bowl is being sanitized, as intended.

An object of the present invention is to provide a method of automatically sanitizing a toilet bowl with each flush.

Another object of the invention is to provide visual color which persists in the toilet bowl water between flushes, i.e. the color is not bleached to a colorless state or oxidized to a different color between flushes.

Another object of the invention is to provide, by a visual color signal, a means by which the consumer will know when a new supply of sanitizing agent needs to be provided for the toilet.

Another object of the invention is to provide an article of manufacture which is designed for carrying out the method of the invention.

DISCLOSURE OF INVENTION

The present invention relates to a method of treating a flush toilet which comprises a flush tank and a bowl, with a hypochlorite sanitizing agent each time the toilet is flushed, and providing a persistent color to the bowl water between flushes. The said method comprises the step of dispensing from separate dispensing means, into the flush water;

A. an aqueous solution of a compound which produces hypochlorite ions in aqueous solution, and
B. a solution of a dye selected from the group consisting of FD&C Blue No. 1 and FD&C Green No. 3;

the amounts of Component A and Component B respectively, being such as to produce a concentration of available chlorine of from about 2 to about 10 ppm, a concentration of dye of from about 0.5 to about 5 ppm and a ratio of available chlorine to dye of from about 2:1 to 6:1 in the bowl water after completion of the flush, the pH of the bowl water being from about 8 to about 9.5 after completion of the flush when the dye is FD&C Blue No. 1 and the pH of the bowl water being from about 8.5 to about 9.5 after the flush when the dye is FD&C Green No. 3.

All ratios and percentages herein are "by weight" unless specified otherwise.

The present invention also relates to an article of manufacture which is useful in carrying out the aforedescribed method.

The Sanitizing Agent

The sanitizing agent of the present invention can be any compound which provides the hypochlorite ion (OCl$^-$) in aqueous solution. Such compounds include alkali metal and alkaline earth metal hypochlorites, hypochlorite addition products, chloramines, chlorimines, chloramides, and chlorimides. Specific examples of compounds of this type include sodium hypochlorite, potassium hypochlorite, lithium hypochlorite, calcium hypochlorite, calcium hypochlorite dihydrate, monobasic calcium hypochlorite, dibasic magnesium hypochlorite, chlorinated trisodium phosphate dodecahydrate, potassium dichloroisocyanurate, sodium dichloroisocyanurate, sodium dichloroisocyanurate dihydrate, 1,3-dichloro-5,5-dimethylhydantoin, N-chlorosulfamide, Chloramine T, Dichloramine T, Chloramine B, and Dichloramine B. Preferred sanitizing agents are calcium hypochlorite, lithium hypochlorite and mixtures thereof. A particularly preferred sanitizing agent composition suitable for use in the practice of the present invention is described in the commonly assigned U.S. Patent Application of John Daniel Nyquist entitled DISINFECTING COMPOSITION, Ser. No. 897,478, filed Apr. 18, 1978, abandoned in favor of U.S. patent application Ser. No. 030,975, filed Apr. 18, 1979 said patent application being incorporated herein by reference. The composition described in the Nyquist application is a compacted cake comprising lithium hypochlorite and calcium hypochlorite in a ratio of lithium hypochlorite:calcium hypochlorite of from about 0.58:1 to about 0.17:1, by weight.

By virtue of the strong oxidizing power of the hypochlorite ion, it is highly effective in bleaching stains, breaking down and removing soils and killing microorganisms, thereby providing effective sanitizing action to the toilet bowl.

The amount of hypochlorite-providing compound dispensed to the toilet in the process of the invention can vary, but preferably should be sufficient to provide from about 2 to about 10 ppm (more preferably from about 3 to about 8 ppm) available chlorine in the bowl water after completion of the flush. The sanitizing agent can be formulated as an aqueous liquid if it is to be dispensed from a dispensing means designed to receive liquids. The sanitizing agent can also be formulated into the form of a solid cake for use in dispensing means which are designed to receive a cake of solid material (see description of dispensing means below). The level of available chlorine in the bowl water can be measured by well-known methods such as the DPD Ferrous Titrametric Method or the Stabilized Neutral Orthotolidine Method, described, respectively, at pages 129 and 126 of Standard Methods for the Examination of Water and Wastewater, 13th Ed., published by American Public Health Association.

In addition to the hypochlorite-producing compound, the sanitizing agent composition can contain diluent materials such as inorganic salts, e.g., sodium sulfate, sodium chloride, etc. For sanitizer cakes, such as those disclosed in the Nyquist application supra, it has been found that sodium silicate is a particularly desirable diluent salt. Sodium silicate not only serves as a diluent, but it also affects the solubility of the cake so as to cause a more uniform release of hypochlorite over the life of the cake. The sodium silicate is desirably used at a weight ratio of about 0.1 to about 0.5 parts sodium silicate to 1 part of the combination of lithium hypochlorite/calcium hypochlorite.

Dyes

A water-soluble, bleach-resistant dye is an essential feature of the present invention. The dye should be soluble to the extent of at least 0.01% by weight in water at 25° C. The dye should be one which is sufficiently resistant to attack by hypochlorite that it will not be oxidized to a different color or to a colorless state (at the respective hypochlorite and dye concentrations specified herein) during the time intervals between flushing of the toilet. For toilets in homes (which is the area of primary interest for the present invention) the typical time intervals between flushes range from a few minutes up to about eight hours. Accordingly, the dyes of the present invention are chosen to be sufficiently resistant to hypochlorite that the solution of the dye in the toilet bowl will not be oxidized to a different color or to a colorless state by the hypochlorite in the bowl for a time period of up to about eight hours. The dyes which have been found to be satisfactory for use in the present invention are FD&C Blue No. 1, (C.I. 42090) and FD&C Green No. 3 (C.I. 42053). C.I. refers to the Color Index listing number. Both of these dyes produce a blue color in the toilet bowl when used according to the present invention. These two dyes have the following structures:

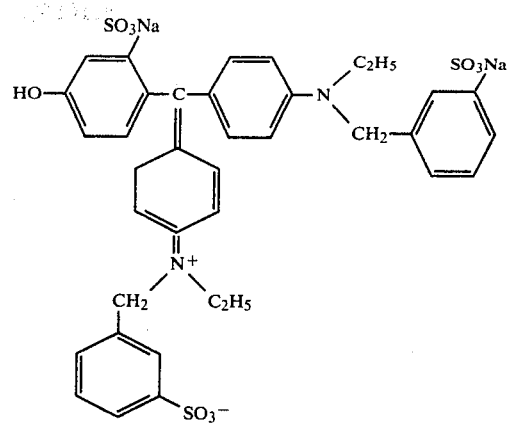

FD&C Green No. 3

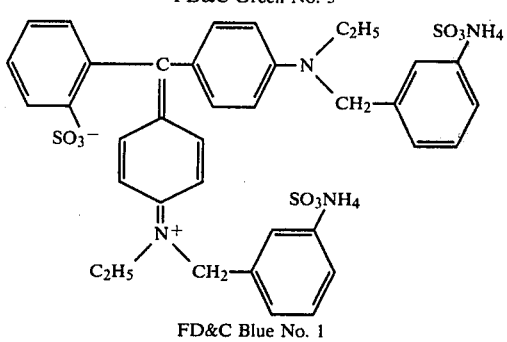

FD&C Blue No. 1

These dyes are not completely stable to attack by hypochlorite; however, they are sufficiently resistant to attack so as to adequately serve the purposes of the present invention. When there is a long time interval between flushes (e.g., several hours) there will be some fading of the color in the bowl water, due to slow attack by the hypochlorite on the dye, but the water will not change color (e.g., from blue to purple), nor will it become colorless.

The amount of dye dispensed to the toilet in the process of the invention will depend on the color intensity desired and the amount of sanitizing agent dispensed into the toilet with the dye. Generally, the amount of dye dispensed will be sufficient to produce a dye concentration of from about 0.05 to about 5 ppm, preferably from about 0.5 ppm to about 1.5 ppm in the toilet bowl. Generally, the dye should be present in a ratio of available chlorine:dye of from 2:1 to about 6:1. Dye concentration and ratios herein are based upon the amount of the actual dye compound, unless specified otherwise. Dyes are normally sold in the form of mixtures of dye compound and inert diluent. FD&C Blue No. 1 is about 90% actual dye and FD&C Green No. 3 is about 90% actual dye.

Optionally, the dyes used in the present invention can be formulated into compositions containing other ingredients which it is desired to dispense into the toilet bowl, such as, for example, pH control agents, surfactants, sequestering agents, perfumes, and diluents such as water, organic solvents such as ethanol, and organic or inorganic salts such as sodium sulfate, sodium chloride and sodium acetate.

To achieve the desired level of color stability in the toilet bowl, the bowl water should have a pH of from about 8.5 to 9.5 when the dye is FD&C Green No. 3 and from about 8.0 to 9.5 when the dye is FD&C Blue No.

1. Most household tap water falls into this range. However, for situations where the tap water has a pH below the desired range, an alkaline salt such as sodium carbonate or trisodium phosphate can be incorporated into the dye compositions (or sanitizing agent compositions) to bring the bowl water to the desired pH range. Conversely, if the pH is above the desired range, an acidic material such as citric acid can be incorporated into the dye compositions for pH adjustment. The amount of alkaline or acidic material to be used will depend upon the size of the pH adjustment required.

Surfactants can provide enhanced sanitizing performance through breakup and emulsification of soils, and also provide some sudsing in the toilet bowl, which may be aesthetically desirable. Perfumes provide a pleasant smell to the area surrounding the toilet and also help to obscure the "bleach" smell of the sanitizing agent. Sequestrants aid soil removal by sequestration of multivalent metal ions.

When the dyes herein are formulated with surfactants, the resulting compositions will generally comprise from about 5% to about 99% surfactant and from about 0.2% to about 15% dye. Perfumes will normally be used at levels of up to about 25% and inert diluents at levels up to about 90%. Sequestering agents such as potassium pyrophosphate, sodium tripolyphosphate and ethylenediamine tetraacetate can be used at levels up to about 25%. Potassium pyrophosphate and sodium tripolyphosphate are examples of sequestering agents which are also alkaline, and therefore may also function as pH control agents in the present invention.

Compositions comprising the dye and a surfactant and/or other ingredients can be conveniently pressed into the form of a cake for use in dispensers which are designed to receive a cake of solid material (see description of dispensing means, below). Such cakes can be made by extrusion or hydraulic stamping, or by pouring a melt of the composition into a mold and solidifying the composition by cooling.

If it is desired to use a dispensing means which is designed to receive liquids, the dye and any optional ingredients such as surfactants, etc., can be formulated into liquid compositions.

Anionic surfactants operable in compositions suitable for use in practicing the present invention can be broadly described as the water-soluble salts, particularly the alkali metal salts, of organic sulfuric acid reaction products having in their molecular structure an alkyl or alkaryl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic surfactants which can be employed in the practicing of the present invention are the sodium or potassium alkyl sulfates, especially those obtained by sulfating the higher alcohols ($C_8$–$C_{18}$ carbon atoms) produced by reducing the glycerides of tallow or coconut oil; sodium or potassium alkyl benzene sulfonates, in which the alkyl group contains from about 9 to about 15 carbon atoms, (the alkyl) radical can be a straight or branched aliphatic chain); paraffin sulfonate surfactants having the general formula $RSO_3M$, wherein R is a primary or secondary alkyl group containing from about 8 to about 22 carbon atoms (preferably 10 to 18 carbon atoms) and M is an alkalimetal, e.g., sodium or potassium; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about 1 to 10 moles of ethylene oxide; sodium or potassium salts of alkyl phenol ethylene oxide ether sulfates with about 1 to about 10 units of ethylene oxide per molecule and in which the alkyl radicals contain from about 8 to about 12 carbon atoms; the reaction products of fatty acids esterified with isethionic acid and neutralized with sodium hydroxide where, for example, the fatty acids are derived from coconut oil; sodium or potassium salts of fatty acid amides of a methyl tauride in which the fatty acids, for example, are derived from coconut oil and sodium or potassium $\beta$-acetoxy- or $\beta$-acetamido-alkanesulfonates where the alkane has from 8 to 22 carbon atoms.

Nonionic surfactants which can be used in practicing the present invention can be of three basic types—the alkylene oxide condensates, the amides and the semipolar nonionics.

The alkylene oxide condensates are broadly defined as compounds produced by the condensation of alkylene oxide groups (hydrophilic in nature) with an organic hydrophobic compound, which can be aliphatic or alkyl aromatic in nature. The length of the hydrophilic or polyoxyalkylene radical which is condensed with any particular hydrophobic group can be readily adjusted to yield a water-soluble-compound having the desired degree of balance between hydrophilic and hydrophobic elements.

Examples of such alkylene oxide condensates include:

1. The condensation products of aliphatic alcohols with ethylene oxide. The alkyl chain of the aliphatic alcohol can either be straight or branched and generally contains from about 8 to about 22 carbon atoms. Examples of such ethoxylated alcohols include the condensation product of about 6 moles of ethylene oxide with 1 mole of tridecanol, myristyl alcohol condensed with about 10 moles of ethylene oxide per mole of myristyl alcohol, the condensation product of ethylene oxide with coconut fatty alcohol wherein the coconut alcohol is a mixture of fatty alcohols with alkyl chains varying from 10 to 14 to carbon atoms and wherein the condensate contains about 6 moles of ethylene oxide per mole of alcohol, and the condensation product of about 9 moles of ethylene oxide with the above-described coconut alcohol. Examples of commercially available nonionic surfactants of this type include Tergitol 15-S-9 marketed by the Union Carbide Corporation, Neodol 23-6.5 marketed by the Shell Chemical Company and Kyro EOB marketed by the Proctor & Gamble Company.

2. The polyethylene oxide condensates of alkyl phenols. These compounds include the condensation products of alkyl phenols having an alkyl group containing from about 6 to about 12 carbon atoms in either a straight chain or branched chain configuration, with ethylene oxide, the said ethylene oxide being present in amounts equal to 5 to 25 moles of ethylene oxide per mole of alkyl phenol. The alkyl substituent in such compounds can be derived, for example, from polymerized propylene, diisobutylene, octene, or nonene. Examples of compounds of this type include nonyl phenol condensed with about 9.5 moles of ethylene oxide per mole of nonyl phenol, dodecyl phenol condensed with about 12 moles of ethylene oxide per mole of phenol, dinonyl phenol condensed with about 15 moles of ethylene oxide per mole of phenol, di-isooctylphenol condensed with about 15 moles of ethylene oxide per mole of phenol. Commercially available nonionic surfactants of this type include Igepal CO-610 marketed by the GAF Corporation; and Triton X-45, X-114, X-100 and X-102, all marketed by the Rohm and Haas Company.

3. The condensation products of ethylene oxide with a hydrophobic base formed by the condensation of propylene oxide with propylene glycol. The hydrophobic portion of these compounds has a molecular weight of from about 1500 to 1800 and of course exhibits water insolubility. The addition of polyoxyethylene moieties of this hydrophobic portion tends to increase the water-solubility of the molecule. Examples of compounds of this type include certain of the commercially available Pluronic surfactants marketed by the Wyandotte Chemicals Corporation.

4. The condensation products of ethylene oxide with the product resulting from the reaction of propylene oxide and ethylene diamine. The hydrophobic base of these products consists of the reaction product of ethylene diamine and excess propylene oxide, said base having a molecular weight of from about 2500 to about 3000. This base is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds marketed by the Wyandotte Chemicals Corporation.

Examples of the amide type of nonionic surfactants include the ammonia, monoethanol and diethanol amides of fatty acids having an acyl moiety of from about 8 to about 18 carbon atoms. These acyl moieties are normally derived from naturally occurring glycerides, e.g., coconut oil, palm oil, soybean oil and tallow, but can be derived synthetically, e.g., by the oxidation of petroleum, or by hydrogenation of carbon monoxide by the Fischer-Tropsch process.

Examples of the semi-polar type of nonionic surfactants are the amine oxides, phosphine oxides and sulfoxides. These materials are described more fully in U.S. Pat. No. 3,819,528, Berry, issued June 25, 1974, and incorporated herein by reference.

Ampholytic surfactants which can be used in practicing the present invention can be broadly described as derivatives of aliphatic amines which contain a long chain of about 8 to about 18 carbon atoms and an anionic water-solubilizing group, e.g., carboxy, sulfo and sulfato. Examples of compounds falling within this definition are sodium-3-dodecylamino-propionate, sodium-3-dodecylamino propane sulfonate, and dodecyl dimethylmmonium hexanoate.

Zwitterionic surfactants which can be used in practicing the present invention are broadly described as internally-neutralized derivatives of aliphatic quaternary ammonium and phosphonium and tertiary sufonium compounds, in which the aliphatic radical can be straight chain or branched, and wherein one of the aliphatic substituents contains from about 8 to about 18 carbon atoms and one contains an anionic water-solubilizing group, e.g., carboxy, sulfo, sulfato, phosphato, or phosphono.

Cationic surfactants which can be used in practicing the present invention include stearyl dimethyl benzyl ammonium chloride, coconut diemthyl benzyl ammonium chloride, cetyl pyridinium chloride and cetyl trimethyl ammonium chloride.

Bleach-stable (i.e., hypochlorite-stable) surfactants which are especially resistant to oxidation are the alkyl sulfates and paraffin sulfonates. Alkyl sulfates are the water-soluble salts of sulfated fatty alcohols containing from about 8 to about 18 carbon atoms in the alkyl group. Examples of suitable alcohols which can be employed in alkyl sulfate manufacture include decyl, lauryl, myristyl, palmityl and stearyl alcohols and the mixtures of fatty alcohols derived by reducing the glycerides of tallow and coconut oil.

Specific examples of alkyl sulfate salts which can be employed in the instant surfactant/dye compositions include sodium lauryl alkyl sulfate, sodium stearyl alkyl sulfate, sodium palmityl alkyl sulfate, sodium decyl alkyl sulfate, sodium myristyl alkyl sulfate, potassium lauryl alkyl sulfate, potassium stearyl alkyl sulfate, potassium decyl sulfate, potassium palmityl alkyl sulfate, potassium myristyl alkyl sulfate, sodium dodecyl sulfate, potassium dodecyl sulfate, potassium tallow alkyl sulfate, sodium tallow alkyl sulfate, sodium coconut alkyl sulfate, potassium coconut alkyl sulfate and mixtures of these surfactants. Highly preferred alkyl sulfates are sodium coconut alkyl sulfate, potassium coconut alkyl sulfate, potassium lauryl alkyl sulfate and sodium lauryl alkyl sulfate.

Paraffin sulfonate surfactants have the general formula $RSO_3M$, wherein R is a primary or secondary alkyl group containing from about 8 to about 22 carbon atoms (preferably 10 to 18 carbon atoms) and M is an alkali metal, e.g., sodium or potassium. Paraffin sulfonate surfactants and methods for their preparation are well known in the art. They may be prepared, for example, by reaction of hydrocarbons with sulfur dioxide, oxygen and a sulfonation reaction initiator. Alternatively, they may be prepared by reacting an alkene and a sodium bisulfite under suitable radiation or catalystsis, as disclosed in British Pat. No. 1,451,228 published Sept. 29, 1976, and hereby incorporated herein by reference. Paraffin sulfonate surfactants are commercially available, e.g., from Farbwerke Hoechst A. G.

Preferred paraffin sulfonates herein are secondary paraffin sulfonates. Examples of specific paraffin sulfonates herein are:
Sodium-1-decane sulfonate;
Potassium-2-decane sulfonate;
Lithium-1-dodecane sulfonate;
Sodium-6-tridecane sulfonate;
Sodium-2-tetradecane sulfonate;
Sodium-1-hexadecane sulfonate;
Sodium-4-octadecane sulfonate;
Sodium-3-octadecane sulfonate.

Normally, the paraffin sulfonates are available as mixtures of individual chain lengths and position isomers, and such mixtures are suitable for use herein.

Dispensing Means

In order to provide automatic sanitizing of the toilet bowl in accordance with the present invention, it is essential that the hypochlorite sanitizing agent and the dye, in the form of relatively concentrated solutions, be dispensed into the flush water each time the toilet is flushed.

It is within the contemplation of the present invention that the concentrated solution of one of the components (i.e., either the dye or the sanitizing agent) be dispensed into the flush tank during the refill after a flush (thereby forming a dilute solution of one component in the flush water which is stored in the tank between flushes) and that the concentrated solution of the other component be dispensed into this treated flush water during the time it is flowing from the tank to the bowl during the next succeeding flush. Dispensing means which operate to dispense solutions into a toilet tank during the time it is refilling are described, for example, in U.S. Pat. Nos. 1,798,080, Lebegue, issued Mar. 24, 1931; 3,339,801, Hronas, issued Sept. 5, 1967; and 3,121,236, Yadro et al., issued Feb. 18, 1964.

It is preferred that both of the concentrated solutions be dispensed into the flush water on the downflush, i.e., that they be dispensed into the flush water during the time the flush water is flowing from the tank into the bowl. In this preferred mode of operation, it is additionally preferred that the dispensing of the hypochlorite and dye should occur near the end of the flush in order to avoid wastage of dye and hypochlorite and to keep to a minimum the time of contact between the concentrated solutions of dye and hypochlorite before they enter the bowl. The respective dispensing means for the hypochlorite and dye solutions should preferably be positioned relative to each other in the toilet tank so that these concentrated solutions will be diluted by flush water during the flush before they come into contact with each other, i.e., intimate mixture of streams of the two concentrated solutions in the flush tank should preferably be avoided. Dispensing means for automatically dispensing solutions of chemicals into the flush water during the down-flush are well known in the art. U.S. Pat. No. 3,504,384, Radley et al., issued Apr. 7, 1970, discloses a dual dispenser for separately dispensing a detergent/dye solution and a hypochlorite solution into the flush water during the flush. Water from the flush tank flows into the respective dispenser chambers as the tank fills after a flush, where it comes into contact with a solid detergent/dye composition and a solid hypochlorite-producing composition in the respective chambers. During the interval between flushes, relatively concentrated solutions of the hypochlorite and detergent/dye compositions form in the respective chambers, and these solutions are discharged into the flush water on the next flush. It should be noted that the inlet and outlet ports of the dispenser chambers in the Radley et al. dual dispenser are not closed between flushings, and therefore there is opportunity for ingredients in the respective concentrated solutions in the chambers to diffuse into the tank water between flushes, whereby there is also opportunity for ingredients from one dispenser chamber to ultimately find their way into the solution in the other dispenser chamber. The longer the time interval between flushes, the more likelihood there is that some portion of the contents of the two dispenser chambers will have an opportunity to come into contact with each other before they are dispensed into the flush water on the next flush. While dispensing devices of the type disclosed in Radley et al. can be used in the present invention, they are not preferred. It is preferred in the present invention that the dye and sanitizing agent be substantially completely isolated from the tank water (and, therefore, from each other) during the quiescent period between flushes. This isolation can be accomplished in the dispensing means by providing a blocking means such as an air bubble or a mechanical seal which, during the period between flushes, blocks the ports by which liquid flows into and out of the dispensing means. Depending on the type dispensing means used, and the materials used in constructing it, complete isolation of the concentrated solutions from the tank water may not always be possible since some small amount of solution may escape by capillary action, imperfect sealing of the inlet and outlet ports, etc.

Dispensers which completely or substantially completely isolate their contents from the tank water during the quiescent period between flushes are known to the art and are the preferred type for use in the present invention. Such dispensers are disclosed, for example, in U.S. Pat. No. 3,831,205, issued Aug. 27, 1974, to Foley; U.S. Pat. No. 3,341,074, issued Sept. 12, 1967, to Panutti; U.S. Pat. No. 4,036,407, issued July 19, 1977, to Slone; U.S. Pat. No. 4,171,546, Dirksing, issued Oct. 23, 1979; and U.S. Ser. No. 897,469, Dirksing, entitled PASSIVE DOSING DISPENSER EMPLOYING TRAPPED AIR BUBBLE TO PROVIDE AIRLOCK, filed Apr. 18, 1978, now abandoned in favor of U.S. patent application Ser. No. 002,524, filed Jan. 11, 1979. All of the foregoing patents and applications are incorporated herein by reference.

Preferably, the amount of sanitizing composition placed in the sanitizing composition dispensing means should be chosen so as to last at least as long as (i.e., through at least as many flushes as) the amount of dye composition in the dye composition dispensing means. When the consumer no longer sees any color appear in the bowl when flushing the toilet, this indicates that the bowl is no longer being sanitized and it is time to replace the system (dye and sanitizer).

Preferably the dispensers used in the practice of the present invention are of the type which are designed to receive a solid composition. Such dispensers are placed below the high water line of the toilet flush tank. When the toilet tank is filling water flows into the dispenser, where a concentrated solution is formed by contact between the composition and the water which is inside the dispenser. When the toilet is flushed the concentrated solution is discharged into the flush water as it is flowing from the tank. Dispensers of this general type are exemplified by those disclosed in U.S. Pat. No. 3,831,205, Foley, U.S. Pat. No. 4,171,546 Dirksing, and Application Ser. No. 897,469, Dirksing, all incorporated by reference above. Two dispensers of this general type, (either having the same design or a different design from each other), can preferably be fabricated into a single article which can be placed into the toilet tank, the one dispenser containing the solid sanitizing composition and the other containing the solid dye composition. Accordingly, the present invention also encompasses an article of manufacture designed for placement below the high water line of the flush tank of a toilet, said article comprising two dispensing means (i.e. dispensers), the first dispensing means containing a solid composition which is soluble in water and comprises a compound which provides hypochlorite ions in aqueous solution, and a second dispensing means containing a solid composition which is soluble in water and which contains a dye selected from the group consisting of FD&C Blue No. 1 and FD&C Green No. 3, said first dispensing means and second dispensing means each having means for receiving water from the flush tank when said flush tank refills after a flush and for maintaining said receiving water in contact with the respective solid compositions in said first and second dispensing means during the quiescent period between flushes so as to form concentrated solutions of said compositions in said respective dispensing means between flushes, said first dispensing means and second dispensing means having means for retaining said concentrated solutions in substantial isolation from each other and from the body of water in the flush tank during the quiescent period between flushes, said first dispensing means and said second dispensing means each having means for releasing said concentrated solutions into the water in the flush tank when said water flows from the tank during flushing. When this article is placed in the flush tank of a toilet it is positioned in a manner such that the means for receiving water and the means for releasing concentrated solutions in both of the respective dispensing means are below the high water line of the flush tank.

The present invention will be illustrated by the following example.

EXAMPLE

A solid, compacted sanitizing composition cake was prepared by dry-mixing FORM-2 lithium hypochlorite (30% LiOCl), as available from Lithium Corporation of America, Bessemer City, North Carolina, with HTH calcium hypochlorite [70% Ca(OCl)$_2$], as available from Olin Mathieson Chemical Corp., NaCl and Na$_2$SO$_4$ in the proportions hereinafter set forth and subjecting the granular mixture to a compaction pressure of about 2.5 tons per square inch on a Stokes Model R Tablet Press:

| Ingredient | % By Weight |
| --- | --- |
| LiOCl (Form 2) | 24.7 |
| HTH [70% Ca(OCl)$_2$] | 38.8 |
| NaCl | 27.1 |
| Na$_2$SO$_4$ | 9.4 |
| | 100.0 |

This composition had a LiOCl:Ca(OCl)$_2$ weight ratio of about 0.27:1, and an available chlorine level (AvCl$_2$) of about 36% to about 37%. The cake had a specific gravity of about 1.7 and dimensions of about 3.5 inches by about 1.5 inches by about 0.625 inches.

A solid, compacted cake containing dye was prepared by mixing the ingredients hereinafter set forth in a batch amalgamator, followed by milling and then extrusion to form a rectangular slab having dimensions of about 3.625 inches in width by about 2.0 inches in height by about 0.5 inches thick, and a specific gravity of about 1.1.

| Ingredient | % By Weight |
| --- | --- |
| Sodium paraffin sulfonate (Hostapur, approximately 84% active, as available from American Hoechst, Somerville, N.J.) | 81.6 |
| FD&C Green No. 3 Dye | 4.5* |
| NaCl | 2.9 |
| Perfume | 11.0 |
| | 100.0 |

*The dye sample contained about 10% diluent, therefore, the actual dye level was about 4.05%.

This dye cake was thereafter coated with talcum powder to prevent it from sticking to the sides of the dispensing apparatus.

The solid sanitizer cake and dye cake were incorporated, respectively, into separately dispensing compartments of a dual dispensing apparatus which was vacuum thermoformed in two segments from 0.015 inch thick polyvinyl chloride. The configuration of the integrally formed dual compartment dispenser was such that the dye cake was placed vertically overhead the sanitizer cake. The portion of the dispensing apparatus housing the dye cake was of a configuration generally similar to those described in connection with FIGS. 1 and 15 of the aforementioned patent application of Robert S. Dirksing, Ser. No. 897,469, filed Apr. 18, 1978, while the portion of the dispensing apparatus housing the sanitizer cake was of a configuration generally similar to that described in connection with FIG. 12 of the aforementioned U.S. Pat. No. 4,171,546, Dirksing, issued Oct. 23, 1979. These separate portions of the dispensing apparatus (actually two separate dispensing means) produce concentrated solutions, respectively, of the sanitizer composition and dye composition in water which enters the apparatus when the toilet tank is filling after a flush. The respective dispensing means serve to substantially isolate the concentrated solutions from each other and from the tank water during the period between flushes, although a very small amount of dye solution was found to migrate into the flush tank between flushes. The positioning of the respective dispensing means of the dual dispenser is such as to prevent mixing of the dispensed sanitizer and dye solutions during the flush until they have been diluted with flush water. The measuring cavity and inlet conduit of the sanitizer-containing portion of the dual dispenser is so sized that approximately 9 cubic centimeters of sanitizer-containing solution is dispensed with each flush cycle of the toilet. The dye-containing portion of the dispenser is so sized that approximately two cubic centimeters of dye-containing solution is dispensed into the flush water as it leaves the tank during each flush cycle of the toilet.

The aforedescribed exemplary embodiment of a dual dispenser for carrying out the cleansing and disinfecting method of the present invention provides an excellent release of both the sanitizer-containing solution and the surfactant/dye-containing solution throughout the life of the unit.

A conventional toilet comprising a flush tank and a bowl was equipped with this type dual dispenser by placing the dispenser into the tank at a depth such that the inlet and outlet ports of both dispensing means were below the high water mark of the tank. Over a 2-day period the toilet was flushed at predetermined time intervals during each day. Observations of color and determinations of available chlorine levels in the bowl just prior to flushing and immediately after flushing were made periodically. The toilet was flushed a total of 22 times. The first six flushes are required to fully prime the dispensing means for the hypochlorite sanitizer. Accordingly, on the first six flushes the amount of hypochlorite delivered to the bowl was lower than desired. After the sixth flush, color observations and available chlorine determinations were made on 11 of the remaining flushes. Color was graded on a 0–10 scale, 0 indicating no preceptible color in the bowl water, and the numbers from 1 to 10 indicating increasing intensity of blue color. The water supply used for flushing had a pH of 8.5.

Results of this experiment are shown in the following table. The experiment was run in duplicate and the results reported are the average of the duplicate runs.

| Day | Time of Flush | AvCl$_2$ Before Flush ppm | AvCl$_2$ After Flush ppm | Color Before Flush | Color After Flush |
| --- | --- | --- | --- | --- | --- |
| 1 | 8:05 AM | 0 | 0 | — | 5 |
|   | 8:10 | 0 | 0 | 5 | 4.5 |
|   | 8:15 | 0 | 1 | 4.5 | 4.5 |
|   | 8:20 | 1 | 1 | 4.5 | 5.5 |
|   | 10:00 | 1 | 1 | 5 | 6 |
|   | 2:00 PM | 0.5 | 0.5 | 5.5 | 5 |
|   | 2:30 | 0.5 | 3 | 5 | 4.5 |
|   | 4:30 | 2.5 | 3 | 4 | 4 |
|   | Note* | | | | |
| 2 | 12:15 AM | 2 | 2 | 4 | 3.5 |
|   | 8:05 | 2 | 2 | 2.5 | 3.5 |
|   | 8:10 | 2 | 2.5 | 3 | 5.5 |
|   | 8:15 | 3 | 3 | 4.5 | 3.5 |
|   | 8:20 | 2.5 | 2.5 | 3.5 | 3.5 |
|   | 10:00 | 4.5 | 4.5 | 2.5 | 5 |
|   | 2:00 PM | 4 | 7.5 | 3.5 | 4.5 |
|   | 2:30 | 4.5 | 4 | 4.5 | 4 |
|   | 4:30 | — | — | — | — |
|   | Note* | | | | |
| 3 | 12:15 AM | 3 | 2 | 3.5 | 4 |
|   | 8:00 | 2 | — | 3 | — |

*Note-Flushes also occured at 4:55, 6:15, 7:45, 9:15 and 10:45 PM on Days 1 and 2, but no color readings or AvCl$_2$ determinations were made at these flushes.

This example illustrates the persistant color, in the presence of hypochlorite, which is provided to the toilet bowl by the present invention during typical time intervals between flushes.

As was noted above, the dispensing means used for the sanitizer cake in this experiment requires about six flushes to become fully primed so as to be capable of delivering the desired levels of hypochlorite to the bowl. If it is desired to deliver the intended level of hypochlorite starting with the first flush, this can be accomplished by forming an additional chamber on the back of the dispensing means and placing in it a 6 gram tablet of sanitizer having the same formula as the sanitizer cake described above. This additional chamber has a volume of approximately 60 cc. and has two 1 inch by ⅜ inch rectangular ports in it which remain in open communication with the water in the toilet tank. When the dispensing device is placed into the toilet tank, water flows into this chamber, and quickly forms a concentrated solution of the sanitizer. Some of the sanitizer solution from the chamber will migrate into the body of tank water, but most of it will remain in the chamber until the flush, when it will leave the chamber and flow into the bowl with the flush water. When the tank refills, water again enters this auxilliary chamber and again forms a concentrated solution of hypochlorite which discharges during the next flush. This expedient provides the intended level of sanitizer for about six flushes, i.e., until the above-described primary dispensing means for sanitizer is primed.

What is claimed is:

1. An article of manufacture designed for placement in the flush tank of a toilet, said article comprising two dispensing means, the first dispensing means containing a solid composition which is soluble in water and comprises a compound which provides hypochlorite ions in aqueous solution, and a second dispensing means containing a solid composition which is soluble in water and which contains a dye selected from the group consisting of FD&C Blue No. 1 and FD&C Green No. 3, said first dispensing means and second dispensing means each having means for receiving water from the flush tank when said flush tank refills after a flush and for maintaining said received water in contact with the respective solid compositions in said first and second dispensing means during the quiescent period between flushes so as to form concentrated solution of said compositions in said respective dispensing means between flushes, said first dispensing means and second dispensing means having means for retaining said concentrated solutions in substantial isolation from each other and from the body of water in the flush tank during the quiescent period between flushes, said first dispensing means and said second dispensing means each having means for releasing said concentrated solutions into the water in the flush tank when said water flows from the tank during flushing, said first and second dispensing means cooperating to produce a concentration of available chlorine of from about 2 ppm to about 10 ppm, a concentration of dye of from about 0.5 ppm to about 5 ppm and a ratio of available chlorine to dye of from about 2:1 to 6:1 in the bowl water after the flush.

2. The article of claim 1 wherein the composition which produces hypochlorite ions in aqueous solution comprises a compound selected from the group consisting of calcium hypochlorite, lithium hypochlorite and mixtures thereof.

3. The article of claim 2 wherein the composition which produces hypochlorite ions in aqueous solution in a compacted cake comprising lithium hypochlorite and calcium hypochlorite in a weight ratio of lithium hypochlorite: calcium hypochlorite of from about 0.58:1 to 0.17:1.

* * * * *